(12) United States Patent
Andle (10) Patent No.: US 7,002,281 B2
(45) Date of Patent: Feb. 21, 2006

(54) MULTI-REFLECTIVE ACOUSTIC WAVE DEVICE

(75) Inventor: Jeffrey C. Andle, Brewer, ME (US)

(73) Assignee: BIODE Inc., Westbrook, ME (US)

( * ) Notice: Subject to any disclaimer, the term of this patent is extended or adjusted under 35 U.S.C. 154(b) by 60 days.

(21) Appl. No.: 10/620,934

(22) Filed: Jul. 16, 2003

(65) Prior Publication Data

US 2005/0012431 A1 Jan. 20, 2005

(51) Int. Cl.
*H01L 41/08* (2006.01)

(52) U.S. Cl. .................................... 310/313 B

(58) Field of Classification Search ............ 310/313 A, 310/313 B, 313 C, 313 D; 333/151–155, 333/193–196

See application file for complete search history.

(56) References Cited

U.S. PATENT DOCUMENTS

| | | | |
|---|---|---|---|
| 4,144,507 A | | 3/1979 | Shreve |
| 4,353,046 A | * | 10/1982 | Hartmann .................. 333/194 |
| 4,598,224 A | * | 7/1986 | Ballato .................. 310/313 R |
| 4,599,587 A | | 7/1986 | Hartman et al. |
| 4,610,680 A | | 9/1986 | LaFleur |
| 4,616,197 A | | 10/1986 | Wright |
| 4,670,681 A | | 6/1987 | Wright |
| 4,679,014 A | * | 7/1987 | Bulst et al. .................. 333/195 |
| 4,731,595 A | | 3/1988 | Wright |
| 4,910,839 A | | 3/1990 | Wright |
| 5,073,763 A | | 12/1991 | Wright |
| 5,117,146 A | | 5/1992 | Martin et al. |
| 5,144,185 A | * | 9/1992 | Yuhara et al. .......... 310/313 B |
| 5,216,312 A | | 6/1993 | Baer et al. |
| 5,235,235 A | | 8/1993 | Martin et al. |
| 5,283,037 A | * | 2/1994 | Baer et al. ............... 422/82.01 |
| 5,321,331 A | | 6/1994 | Baer et al. |
| 5,387,833 A | | 2/1995 | Baer |
| 5,485,052 A | * | 1/1996 | Seki et al. .............. 310/313 B |
| 5,532,538 A | | 7/1996 | Jin et al. |
| 5,793,146 A | | 8/1998 | Wright |
| 6,033,852 A | | 3/2000 | Andle |
| 2002/0173922 A1 | | 11/2002 | Potyrailo |

OTHER PUBLICATIONS

'Saw Resonator 2-Pole Filters', EJ. Staples, J. Wise, J.S. Schoenwald and T.C. Lim, Proc. 234th Ann. Freq. control symposium pp. 273-277, USAERADCOM, Ft. Monmouth, NJ, May 1980.

'Multipole Saw Resonator Filters: Elements of Design and Fabrication', William J. Tanski, 1981 Ultrasonics Symposium pp. 100-104, 0090-5607/81/0000-0100.

'Multipole Saw Resonator Filters', William J. Tanski, 36th Annual Frequency Control Symposium-1982 pp. 400-404.

'1500 MHz Coupled Resonator Filter', M.B. King, L.W. Heep, J.C. Andle, 1987 Ultrasonic Symposium pp. 127-130.

'Reflective Arrays for SAW Resonators', Peter S. Cross, 1975 Ultrasonics Symposium Proceedings, IEEE Cat. No. 75 CHO pp. 994-4SU 241-244.

'A study of the Property and Potential Application of Acoustic-Surface-Wave resonators', G.L. Matthaei, F. Barman, E. B. Savage, and B.P. O'shaughnessy, 1975 Ultrasonics Symposium Proceedings, IEEE Cat. # 75 CHO 994-4SU pp. 284-289.

(Continued)

*Primary Examiner*—Mark Budd
(74) *Attorney, Agent, or Firm*—Shalom Wertsberger; Saltamar Innovations (57) ABSTRACT

An acoustic wave device, which utilizes multiple localized reflections of acoustic wave for achieving an infinite impulse response while maintaining high tolerance for dampening effects, is disclosed. The device utilized a plurality of electromechanically significant electrodes disposed on most of the active surface. A plurality of sensors utilizing the disclosed acoustic wave mode device are also described.

56 Claims, 3 Drawing Sheets

OTHER PUBLICATIONS

'Surface Acoustic Wave Resonators on ST-Quartz', EJ. Staples and R.C. Smyth, 1975 Ultrasonics Symposium Proceedings, IEEE Cat. #75 CHo 994-4SU pp. 307-310.

"UHF Surface Acoustic Wave Resonators", E.J. Staples, 1974 IEEE Frequency Control Symposium, pp. 280-285.

'Surface Acoustic Wave Resonators Constructed of Aluminum on ST Quartz for Use in High Stability Feed Back Osciators', F.G. Marshal, 1975 Ultrasonics Symposium Proceedings, IEEE Cat.#75, CHO 994-4SU pp. 290-292.

'Design and Application of Two-Port SAW Resonators on YZ-Lithium Niobate', Peter S. Cross, William H. Haydal, and Robin S. Smith, Proceedings of the IEEE, vol. 64, No. 5, May 1976, pp. 682-685.

'Synchronous IDT SAW Resonators with Q above 10,000', Peter R. Cross, William R. Shreve, and Tun Sein Tan, 1979 Ultrasonics Syposium pp. 824-829, CHI48-9/79/0000-0824.

'Multimode SAW Resonators—a Method to Study The Optimum Resonator Design' W.H. Haydl, B. Dischler, P. Hiesinger, 19756 Ultrasonics Symposium Proceedings pp. 287-296, IEEE Cat. # 76 CH1120- SSU.

'GHz SAW Resonators', William J. Tanski, 1979 Ultrasonics Symposium pp. 815-823, CH182-9/79-0000-0815.

'SAW Resonators and Coupled Resonator Filters', E.J. Staples and R. C. Smythe, 1976 IEEE Frequency Control Symposium, pp. 322-327.

'The Design of SAW Resonators on Quartz with Emphasis on Tow Ports', William J. Tanski and Herman van de Vaart, 1976 IEEE Ultrasonics Symposium, pp. 260-265.

'Surface Acoustic Wave Resonator Development' J. S. Schoenwald, W. R. Shreve and R.C. Rosenfeld, 1975 IEEE Frequency Control Symposium, pp. 150-157.

"Surface Wave Filters, Design Construction, and Use", to Mathews, (p. 153, Wiley Interscience Publication, John Wiley &Sons, New York, USA).

* cited by examiner

MULTI-REFLECTIVE ACOUSTIC WAVE DEVICE

STATEMENT OF GOVERNMENT INTEREST

The United States Government has rights in this invention pursuant to Contracts No. DE-FG02-97ER82335 and DE-FG02-94ER-81717 awarded by the United States Department of Energy, and Contract No. DAMD17-95C-5033 awarded by the United States Army.

FIELD OF THE INVENTION

This application is directed generally to acoustic wave devices, and more particularly to a piezoelectric device allowing operation through large variations of temperatures and perturbation dampening.

BACKGROUND OF THE INVENTION

Acoustic wave devices have been used extensively in the art as frequency reference resonators, delay lines, and sensors. The oldest acoustic wave device structure is the parallel plate resonator, which consists of a plate of piezoelectric material having substantially flat and parallel polished surfaces, one or both of which support one or more conducting electrodes. When a voltage signal is applied between the electrodes, stress fields induce elastic deformations of the crystal (strain fields). The deformations of the crystal alter the distribution of charge within the crystal and a net flow of charge (a current) exists.

A more advanced acoustic wave device utilizes surface acoustic waves, surface transverse waves, or acoustic plate modes. Those devices are generally known as SAW devices, or as acoustic plate mode devices. Briefly, these devices comprise a substrate of piezoelectric material such as quartz or lithium niobate, or thin films of piezoelectric material, such as zinc oxide, or cadmium sulfide, on a non-piezoelectric substrate. The substrate has at least one active piezoelectric surface area, which is highly polished. Formed on the surface are input and output transducers for the purpose of converting input electrical energy to acoustic energy within the substrate and reconverting the acoustic energy to an electric output signal. The input and output transducers frequently comprise interdigitated transducers each comprising a plurality of interdigitated electrode fingers which are electrically coupled to an input signal, and to an output measurement device respectively. Such transducers are known as IDT (Inter Digitated Transducer) and are typically formed by depositing a thin film of electrically conductive material such as aluminum or gold in the desired shape on the active area. Electrical potential is coupled to the input transducer and induces mechanical stresses in the piezoelectric substrate. The resultant strains propagate along the surface of the substrate to the output transducer, whereby they are converted to output electrical signals. The waves may propagate along the surface of the crystal (surface modes), or through the bulk of the crystal structure (waveguide modes).

When designing an acoustic wave device, one has to consider the size, number, mass, shape, and connection method of the electrodes, as those parameters significantly effect the behavior of the device. The effects of the electrode design are known in the art. However, for simplicity, these specifications will relate to electromechanically insignificant electrode structure to mean that an acoustic wave traveling under a short-circuited transducer containing electromechanically insignificant electrodes, would experience no significant reflective coupling into a reverse-traveling wave due to the periodic perturbations from the nominal surface conditions outside the transducer region. The opposite of electromechanically insignificant electrode structure described above, is naturally the electromechanically significant electrode structure, which means that such reflective coupling would be created and enhanced.

Typically, insignificant electrodes are designed to have a minimum thickness (mass) required by the electrode dimensions to provide adequate conductivity and the ability to affix bond wires. However, as the operating frequency increases, creating mechanically insignificant electrodes becomes harder as the dimensions decrease inversely to the frequency. Furthermore, in piezoelectric materials such as lithium niobate having high piezoelectric coupling, mechanically insignificant electrodes are electrically (and thus electromechanically) significant. However a method of connecting more than one consecutive electrode to the same polarity is known to locally cancel the resulting electromechanical reflections and thus make the electrodes effectively be electromechanically insignificant, even at higher frequencies or in high coupling materials.

It is clear that as the acoustic wave propagation in the crystal is mechanical in nature, changing the environment in which the crystal operates changes the behavior of the crystal, and it follows that the electrical characteristics exhibited by the piezoelectric device change as well. Thus for example, temperature, and/or the medium in which the crystal is suspended, varies the crystal response. Therefore, exposing a driven piezoelectric crystal to contact with a fluid or a polymer material will dampen the wave propagation in the crystal, and change the characteristic response of the device. This change may be used to measure certain characteristics of the fluid, or may be a side effect of polymer films in gas sensing or of the fluid in efforts to measure other properties of said fluid. In this manner a sensitive sensor is created. Sensors may also be made responsive to specific substances. This is done by for example, placing a polymer film on the sensor. If the polymer is sensitive to a specific gas or biological agent for example, the polymer characteristics will change, and with it its effect on the mechanical perturbations in the crystal. Examples of such sensors is taught in U.S. Pat. No. 5,283,037 to Baer et al., in U.S. Pat. No. 5,235,235 to Martin et al., and U.S. Pat. No. 6,033,852b to Andle et al.

The ideal sensor will have a narrow bandwidth, high Q factor, and a well defined behavior change in response to the measured parameter. It will exhibit wide dynamic range, be energy efficient, (both for efficiency's sake, and to limit the need for high amplification with its inherent problems), and operate predictably over a wide range of variation in the ambient environment. Clearly, the sensor must have unique, measurable changes throughout the measurement range, which typically should be as wide as possible.

Feeding an alternating voltage signal into the input transducer of an acoustic wave device will cause periodic deformations in the crystal, and the generated acoustic waves, when incident on the output transducer, will cause a net current effect into the transducer's load impedance. Using a low impedance current measuring device, it is possible to measure the delayed and attenuated replica of an input voltage signal at the output transducer. In an ideal device, a signal introduced into the acoustic wave device will traverse the device only once. However, as the transducers and their respective circuits are not ideal, the current produced in the output transducer, unless delivered to a short-circuit load, will cause regeneration of the input signal, which will cause a regeneration of the signal at the input transducer, and so forth ad infinitum. This reflective phenomenon hinders the design of devices such as acoustic wave delay lines, while other devices such as resonators, take advantage of it.

Figure 1:
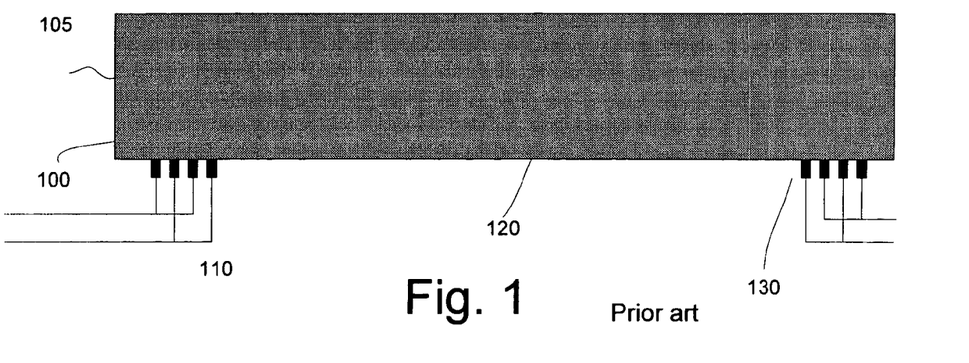
FIG. 1 depicts a simplified diagram of an acoustic wave delay line.

A typical acoustic wave delay line 100 as depicted schematically in FIG. 1, comprises a piezoelectric substrate 105, an input 110 and output 130 transducers deposited on the substrate, and separated by a relatively long passive propagation path 120. As the signal in the output transducer is delayed by the time it takes the periodic deformations to propagate in the crystal, a delay line is formed. The ideal delay line will exhibit a broad bandwidth and minimized reflection, preferably only a single transit between the input and output transducers, in order to achieve the finite impulse response desired from such device. Therefore in order to minimize the ripple and reflections, design criteria calls for making the delay line utilizing the smallest number of electrodes necessary for the desired electrical coupling efficiency, and making the electrodes as small, light, and electrically insignificant as possible, in order to minimize their reflective effects.

Common wisdom in the art also dictates that a very low ripple is an important design goal for delay lines. For example, in the popular book in the field "Surface Wave Filters, Design Construction, and Use", to Mathews, (page 153, Wiley Interscience Publication, John Wiley & Sons, New York, USA) less than ±0.5 dB is desired. Other authorities in the field also indicate this stated design goal, which dictates the use of electromechanically insignificant electrodes. Large number of electrodes or the use of electromechanically significant electrodes, causes triple transit echoes, and also another problem considered undesirable by those skilled in the art, (see Matthews page 156, line 3) of " - - - reflections within a given transducer - - - ". Thus the present state of the art generally teaches that the reflections are significant with as little as 10 electrodes on lithium niobate or 100 electrodes on quartz. Accepted design practices call for reducing the electrodes even below those numbers, to a bare minimum required for appropriate coupling, and reducing the electromechanical significance of the electrode.

In order to further reduce ripple and regeneration effects while using a delay line in a phase coherent circuit, common practice requires a mismatch between the input and output impedances and their respective electrical circuits that will cause an insertion loss of about 20 db between the input and on the output, even in the absence of damping effects. Other methods of reducing the regeneration effects have been taught by using unidirectional transducers often implemented by inserting a reflector, typically made of grating of either metal electrodes or of slots cut out in the piezoelectric substrate, which are designed to be in 180 degrees phase shift of the regenerated signal and thus to cancel it. The phase coherent delay line using bi-directional transducers suffers from low efficiency, which limits the availability of dynamic range needed for sensor applications. The unidirectional transducers are dependent on a critical balance of mechanical reflections and electrical regeneration, which is difficult to maintain over the variations in electrical parameters and insertion loss dynamic range needed for sensor applications. This is, in part, a result of the variable mechanical damping involved, which alters both the required point of balance between reflection and regeneration and the amount of reflection available to balance the regeneration.

From the above discussion it is seen that if the ripple in an acoustic wave device operating as a delay line, can be controlled by the device structure rather than by the external circuitry connected to it, the device will be better suited for sensor applications.

Figure 2:
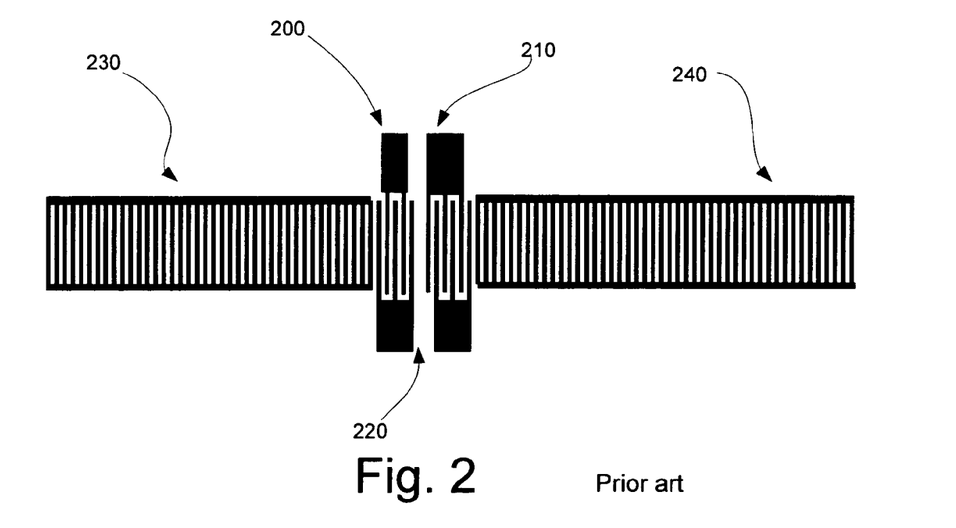
FIG. 2 represents a simplified diagram of an acoustic wave resonator.

Resonators represent another common acoustic wave device type. The resonator is commonly used in oscillator circuits as the timing element in the feedback loop of an oscillator, and similar circuits. Thus the electrical characteristics desired in a resonator call for a very sharp frequency bandwidth, and a very high Q to allow for efficient coupling. As shown in FIG. 2, the typical acoustic wave resonator comprises a piezoelectric crystal, with relatively short, low electrode count, input 200 and output 210 transducers deposited on the crystal. A relatively short resonant cavity 220 is interposed between the transducers. In order to absorb most acoustic waves but enhance the reflection of acoustic waves that are at the resonator frequency, extensive regions of electromechanically significant reflective gratings 230 and 240 are added to the sides of the resonant cavity to act as tuned signal mirrors. The acoustic wave that is trapped between these tuned grating reflectors is multiply reflected with a long propagation path between reflections, and the echoes produce a high Q factor resonance. While most reflections do not add coherently, a standing wave will be created at one or more frequencies of coherent reflection that depends on the grating's relationship to the wavelength. The input transducer drives the standing wave and the output transducer detects that standing wave. Thus the resonator exhibits high energy efficiency, (a high Q factor due to the infinite impulse response), and a very narrow, resonant spike type bandwidth. It should be noted that some resonator design call for a single transducer, and some call for mixing the transducers within the reflective grating (U.S. Pat. No. 4,144,507 to Shreve), but the general behavior and operational principle of the resonator remains the same.

The high Q factor exhibited in a resonator is very desirable for sensor applications. However, when dampening is applied to the conventional resonator, such as by exposing it to a liquid, or depositing a film thereupon, the signal decays rapidly, before it can be reflected back into the transducers a sufficient number of times. Dampening therefore turns the high Q factor resonator in free air, into a very low Q factor device when coated or suspended in other fluids. Because a resonator degrades very rapidly upon dampening from external effects, it is of limited use in sensor applications having substantial damping of acoustic waves.

Additionally, loading a resonator by the like of a polymer film, significantly raises the resonator's typically low insertion loss, often increasing from approximately 7 dB to approximately 20 dB with even light damping. Clearly this causes a reduction in the dynamic range available for a sensor application. This effect has even been observed for relatively high acoustic quality passivation films of silica or silicon nitride.

There is therefore a clear and heretofore unanswered need for an acoustic wave sensor structure which exhibits narrow bandwidth and that offers high energy efficiency without the severe degradation exhibited by the existing structures. The present invention aims to provide such a device.

SUMMARY OF THE INVENTION

At the root of the present invention is the use of a plurality of local reflections in a predetermined and novel manner, to obtain the narrow bandwidth, high efficiency device that can tolerate damping effects while maintaining a usable Q factor and insertion loss, and thus provides a sensor with desirable characteristics. Thus in simplified general terms, the preferred embodiment of the invention provides for a long input transducer and a long output transducer, both having electromechanically significant electrodes, being disposed on or integrated within a substantially periodic reflective grating. The extents of the reflective grating define the device active area. The transducers cover the majority of the active area, and in the most preferable embodiment, a short delay grating is disposed between the transducers without forming a specific resonant cavity to localize acoustic wave energy. It is an integrated part of the reflective grating, typically formed by depositing electrodes thereupon.

When discussing the invention, it should be noted that the term crystal conveys a broad meaning, which extends to piezoelectric crystal as well as any material such as ceramic or a polymer that exhibits piezoelectric or ferroelectric characteristics. It is also recognized that piezoelectric or ferroelectric material is commonly being layered on other, non piezoelectric material, and that the term piezoelectric, or crystal, extends to such materials as well. Other terms of the art such as resonant cavity should also be given their reasonable and customary meaning within the art.

Thus there is provided a multi-reflective acoustic wave device comprising a substrate having at least one layer of uniform thickness piezoelectric substance having at least one substantially flat surface capable of generating, guiding, and detecting an acoustic wave. A reflective grating is deposited on said flat surface having a length along its longitudinal axis, said length defining longitudinal extents of an active area, wherein said active area covered on at least 60% of its longitudinal dimension by electromechanically active elements of said reflective grating, said elements being spaced at substantially periodic intervals commensurating with the wavelength of said acoustic wave, and forming an input transducer and an output transducer, each integrated into said reflective grating, and comprising a plurality of electromechanically active and significant interdigitated electrodes. The input transducer is adapted to induce an acoustic waves, said acoustic wave having a frequency and a vector, and guided by said surface or between said surfaces to travel substantially perpendicularly to said electrodes. A propagation path is interposed between said input and output transducers. The reflective grating is constructed to create an electromechanically significant reflective coupling between the forward and a reverse traveling acoustic wave induced in the piezoelectric substance. The reflectivity of the grating is commonly stated as $(\kappa/K_T)$, wherein $\kappa$ represents the unnormalized reflective coupling (in 1/meters), and is normalized to the fundamental spatial frequency component of the transducer, and $K_T = 2\pi/\lambda$. Reflective gratings have, by definition, a nonzero value of reflectivity, and are further defined to have a minimum reflectivity value.

Preferably, the reflective grating or a portion thereof comprises a plurality of essentially periodically repeating subgroups. Optionally the subgroups are independently weighted. Also preferably, each of the majority of the electrodes in the reflective grating provides a reflectivity of at least 0.1%. The transducers may be unidirectional or bidirectional.

Optionally, the reflective grating further comprises a substantially periodic, electrically inactive reflective structure interposed between said input and output transducers. Preferably, the reflective structure having a length of between 25 and 150 of said periodic intervals. In one embodiment, the reflective structure comprises corrugations in said piezoelectric substance. In another embodiment at least a portion of the reflective grating comprises metal electrodes deposited on the substrate. In another embodiment, at least a portion of reflective grating comprises grooves cut in said substrate. The different methods of creating the reflective grating is a matter of technical choice, and other embodiments, or a combination of embodiments are also contemplated.

If desired, the reflective grating has at least one periodicity variation to introduce a fixed offset in the phase shift between a signal coupled to said input transducer and a corresponding signal induced in said output transducer. At least a portion of said reflective grating optionally comprises dielectric material deposited on said substrate.

Preferably the transducers have a length greater than or equal to 50 of said periodic intervals, or more preferably, greater than 200 intervals. Also preferably, at least the input transducer has a dispersion curve having a stopband with width being between 0.2% and 2% of the nominal design center frequency and essentially centered at a design frequency. The dispersion curve is the relationship between the spatial frequency, $k$, and temporal frequency, $\omega$, of waves propagating under the transducer. The dispersion curve deviates from the ideal form for a bare-crystal, $k=\omega/v$ where $v$ is the constant velocity of the wave, due to the multi-reflective effect. The dispersion curve supports a stopband at $\omega_0$ where $k=K_t$, the width of this stopband being proportional to the reflectivity, $(\kappa/K_t)$, such that the normalized stopband width, $\Delta\omega/\omega_o = 2\kappa/K_t$.

The preferable embodiment further comprises an amplifier circuit coupled between said input and output transducers to form an oscillator.

In another aspect of the invention there is provided a sensor. A sensing face is in mechanical communication with said substrate. An oscillator circuit having an output is coupled to said input transducer; and a sensing circuitry having an output and an input is coupled to said output transducer. A measuring circuitry for measuring at least one parameter of a signal derived from said output transducer.

Preferably, the measuring circuitry comprises a comparator for detecting differences between the output of said oscillator and the output of said sensing circuitry, for detecting differences therebetween, said differences being influenced by exposure of said sensing face to a sensed substance.

Preferably an output from said output transducer is coupled to said oscillator for providing feedback. More preferably, the sensing circuitry and the oscillator are integrated.

The comparator may measure phase difference, power absorption between said input and output transducers, preferably utilizing temperature compensated diode detector, for detecting said power absorption. The comparator may also measure frequency change of the oscillator, induced by changes in the delay time of a signal inputted into said input transducer and outputted from said output transducer, caused by damping and/or stiffening effects of the acoustic plate device. Any combination of voltage, current, phase, and the like may be measured by the comparator.

The sensing face may be on a face opposite to the face carrying the grating, or on the same face. The sensing face may also be adapted for exposure to liquid or gas in a manner allowing damping of a signal propagated within said substrate. An intermediate layer may be deposited on the sensing face, which may comprise a substance sensitive material, chemically structured to change at least one physical property thereof responsive to the presence of predetermined molecules or molecule groups.

In the most preferred embodiment, there is provided a sensor tolerant of viscous dampening comprising an acoustic wave device as described above, further comprising a sensing face in mechanical communication with a piezoelectric substrate. An oscillator circuit having an output coupled to said input transducer. The input and output transducers are each coupled to high efficiency, temperature compensated diode detectors. A comparator for detecting differences is coupled to the diode detectors, for detecting differences therebetween, said differences being influenced by exposure of said sensing face to a sensed substance.

DETAILED DESCRIPTION

Figure 3:
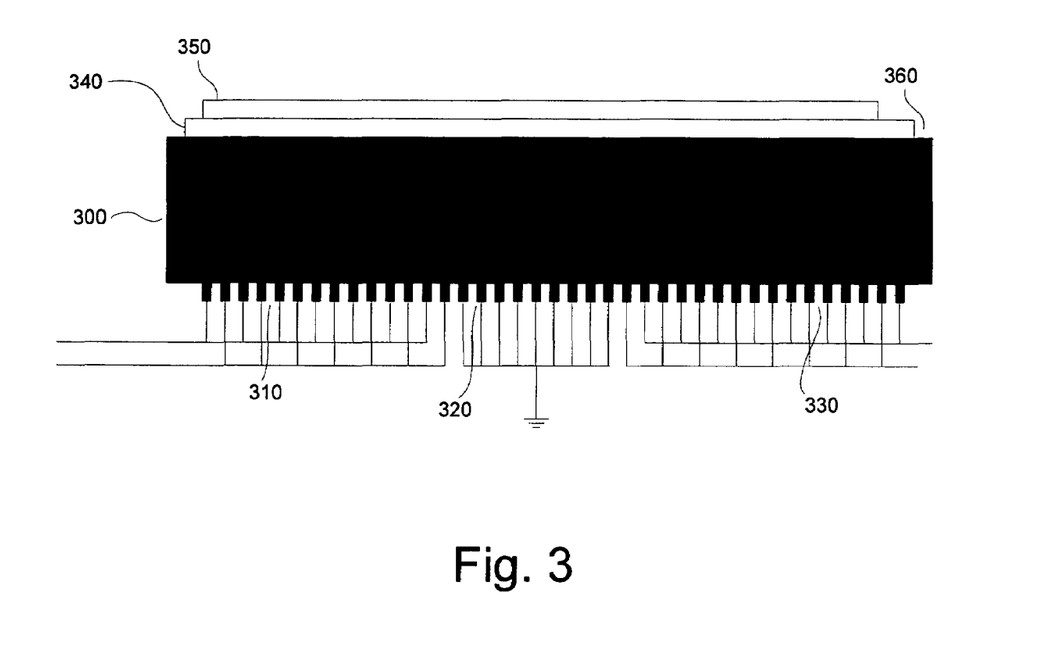
FIG. 3 represents a simplified diagram of an acoustic wave device in accordance with the preferred embodiment of the invention.

Reference is now made to FIG. 3 to provide a description of the preferred embodiment of the present invention, which comprises a structure having a substrate 035 which may be constructed of several layers, or be made of uniform material. At least one layer of the substrate, or all of it, is made of piezoelectric substance having essentially uniform thickness. The piezoelectric substance has at least one substantially flat surface, constructed to guide an acoustic wave. The preferred flat surface is one polished to a flatness having variations that are insignificant compared to the intended wavelength.

A large reflective grating (310, 320 and 330) is deposited on the flat surface. It is substantially periodic within a certain tolerance of the intended wavelength, so that it will continue propogation of an acoustic wave while remaining synchronous with the wave. While the reflective grating is essentially periodic and preferably coherent, it may contain areas without gratings, or other deviation from periodicity and coherence may be introduced to produce desired effects, such as a constant offset to the phase shift for example. Phase shift may also be introduced by spacing the electrodes slightly out of phase with the traveling wavelength.

The extents of the reflective grating define the active area of the device, and the reflective grating elements cover most of the length of the active area.

The reflective grating comprises interdigitated 'electrodes' and 'lands'. It may be constructed by depositing on the piezoelectric surface metal electrodes, dielectric material, conductive material, or any other material that causes periodic perturbation that effect the propagation of a wave via the creation of reflections of the acoustic wave. Alternatively the reflective grating may also be achieved by cutting slots into the piezoelectric material. Material such as metal or dielectric may also be deposited in or on the lands and grooves of the grating. Those methods and their equivalents, including various combinations thereof will be clear to the one skilled in the art.

Electrodes in the grating may be formed in essentially repeating subgroups, which may be individually weighted, or having a uniform weight, to increase the efficiency of signal coupling into the piezoelectric material at desired frequencies while minimizing the efficiency at undesired frequencies. Strategies for weighting such subgroups are well known to one skilled in the art.

The geometry of at least the majority of the grating elements, are designed to be electromechanically significant, meaning generally, to create an electromechanically significant reflective coupling between a forward and a reverse traveling wave supported by the device causing a so-called "stopband" in the dispersion relationship between the wave vector and the frequency, preferably such that the stopband is essentially centered at the design frequency, $\omega_o$, and the width of the stopband. $\Delta\omega$ is given as $$\Delta\omega_k/\omega = 2\kappa/K_I = 4\pi\kappa/\lambda_I,$$

wherein $\omega$ represents the frequency, $\lambda$ represents the wavelength, and $\Delta\omega$ represents the bandwidth. In the preferred embodiment, electromechanically significant implies a structure creating a stopband width in excess of 0.2% of the nominal center frequency for the specific acoustic wave and solid support structure, where practical considerations of mode conversion place an upper limit of 2% on the stopband width. The width of the resulting stopband is specified because it is a governing feature that is readily observed in the device's electrical response and may be specified independently of the specific means of implementation or variations in mathematical definition that differ by factors of $2\pi$ in defining the reflectivity of an electrode or a subgroup. Stopband widths of 0.2% to 2% correspond to reflectivity, $(\kappa/K_I)$, of 0.1% to 1% or "reflectivity per wavelength" $(\kappa\lambda)$ of 0.6% to 6%. Therefore, the reflective grating electrodes create controlled reflections in both the forward and reverse direction, in the vicinity of the electrode.

Input and output transducers are integrated within the reflective gratings. The transducers are dispersive in nature and are constructed to interact with the wave in manner that will cause the wave to have a velocity which is different than the constant velocity expected from the propagation of a given frequency in the crystal (i.e. in the absence of the stopband.) Each transducer covers a large area, typically in excess of 30%, of the active area, and comprises a large number of electromechanically active electrodes. The transducer bandwidth (in the absence of the stopband effect) is designed to be close to the stopband width of the reflective grating (i.e. the bandwidth in which the grating spatial separation causes constructive interaction with the signal). Because of the dispersion, the resulting pass band of the acoustic wave device can be made to be 2 to 10 times more narrow than it would be without the stopband for the same size transducer.

The electromechanically significant electrodes each cause a local reflection in the crystal that propagates some distance along the crystal, which causes perturbations in the electrical efficiency of adjacent electrodes. Therefore the propagated signal becomes practically infinitely reflective over finely distributed short propagation paths between reflections as opposed to the long path length between reflectors of the resonator. Thus the device exhibits a combination between the finite impulse response of the delay line and the infinite impulse response of the resonator. Moreover, the mechanical energy is more evenly distributed along the crystal, and thus the device is capable of transferring more energy along a dampened surface, preventing the severe degradation associated with a resonator. The device also has essentially uniform sensitivity to perturbations along the surface.

By using the structure described above, the reflections that the present state of the art attempts to minimize are effectively controlled and used to provide the relative immunity to propagation loss and maintain the high Q requirements of a sensor.

In order to obtain the desired large feed area and reflection characteristics, the distance between the transducers is smaller than the length of the longer of the two transducers and thus the transducers cover the majority of the active area. The transducer length is measured between the first and last active electrodes and includes the electrodes and the spaces therebetween. The preferred embodiment uses transducers of essentially the same length, and each covers about one third of the active crystal area, or more.

In the preferred embodiment, an intermediate reflective structure 320, preferably electrically inactive, is interposed between the input and output transducers. The intermediate reflective structure is also integrated into the reflective grating. It is preferable that the intermediate reflective structure comprise grounded metal electrodes. Such grounded intermediate grating reduces cross capacitance between the input and output transducers and thus improves the coupling quality of the device. The intermediate structure however is not an essential part of the device.

Therefore in the preferred embodiment substantially all the active area is covered by electrodes of the input transducer 310, output transducer 330, and the optional intermediate grating 320. In contrast to the known delay line in which the propagation path of the intermediate area is mechanically passive, and the electrodes' electromechanical significance is minimized, in the present invention most of the active area is covered by electromechanically active (transducing) electrodes, and the non-driven propagation path is either very small (e.g. a fractional wavelength phase offset) or is electromechanically significant (multi-reflective) by virtue of the electrodes of the intermediate grating. Since the electrodes used are made electromechanically significant, a local reflection is created under each such electrode, and the local reflections are added coherently from the input to the output, providing the required high coupling efficiency. This structure allows the transducers a strong coupling to the crystal and thus increased electrical efficiency, as well as offering the wide operating range required.

While the device may extend laterally from the active area the extended areas are not considered part of the active area as they are not directly in the path of the induced waves from the input to the output transducers. In the preferred embodiment, such extended areas are made absorbent, e.g. by coating the peripheral faces of the crystal in absorbent material. In the preferred embodiment the absorptive material is integrated into the device packaging as a chemically resistant adhesive material.

Use of guard electrodes, i.e. a small number of shorted electrodes placed on the outside edge of a transducer is well known. Such electrodes are used to preserve the continuity of electrical properties of the active electrodes. The guard electrodes may also be used reflect or to absorb the residual wave propagating in the opposite direction to the desired direction of signal propagation. The preferred embodiment of the present invention uses such guard electrodes.

The local reflections enhance the energy coupling efficiency. The signal created under the electrodes is self-propagating and repeatedly reflects between the electrodes and the crystal, and thus the device provides an energy efficiency approaching that of an un-damped resonator. Since practically each electrode creates a local reflection, an infinite number of reflections are created and an infinite impulse response device is created. However, the energy efficiency created by the continual reflection, and the feeding of power into the large area of the transducer, also makes the device relatively immune to severe drops in Q factor typical to the damped resonator without incurring excessive increases in insertion loss. This occurs because the short transit paths between distributed local reflections diminishes the unwanted effects of the damping.

While the output transducer is driven by the acoustic strains and polarization charge variations introduced by the injected input signal, similar local reflections occur in the output transducer, and thus the wave is contained over most area of the crystal.

In the most preferred embodiment, the subgroup structure consists of a simple two-electrode per period transducer having a stopband width of approximately 0.5% on a temperature stable substrate such as quartz. The preferred embodiment has 200 periods in each of the input and output transducers with a 100 period grating between the transducers and approximately 10 periods of reflective grating adjacent to the outer ends of the transducers as "guard electrodes". In this embodiment, $L_{cc}/L_u=1.5$ (wherein $L_{cc}$ is the distance between the center of the transducers and $L_u$ is the equivalent uniform length of the longest of the two transducers) and the stopband width and transducer bandwidth are equal while the electrical efficiency of the structure is maximized relative to any other subgroup structure (e.g. 3-electrode or 4-electrode subgroups or the so-called hopscotch subgroups of group-type unidirectional transducers). The intermediate reflective structure has a reflectance (total reflection coefficient of an incident acoustic wave caused by the entire array of periodic reflective elements) of 90% (−0.9 dB) at its synchronous frequency, but readily transmits acoustic signals near the lower and upper stopband edge. Depending on the substrate material selection, piezoelectric coupling is preferentially enhanced at one stopband edge over the other and the transducers are maximally efficient at generating and detecting acoustic waves. In the preferred embodiments using quartz substrates the preferential efficiency is at the lower stopband edge. The transducer gratings have a reflectance of 99.5% (−0.04 dB) at the synchronous frequency and are still substantially reflective at the stopband edge, helping to trap the acoustic energy and enhancing the overall electrical efficiency of the device without localizing the acoustic energy to a discrete resonant cavity. While the above describes preferred embodiments, it should be noted that embodiments with transducers of lengths as low as 50, or as high as 200, of the periodic intervals, are also feasible, while staying within the desired 0.5% to 2% stopband range of the nominal design center frequency. It should be also noted that the stopband range is also a design consideration and the invention will operate well at other stopband ranges, such as of 0.2%–3% for example. Similarly, the intermediate grating occupies preferably the range of between 25 and 150 of the periodic intervals, but will operate at other intervals. Those skilled in the art will recognize the precise selection of ranges and lengths such as those mentioned above are a matter of technical choice and may need to be tailored to specific design requirements such as cost, operating ranges, and the like.

In experiments it was found that while the common insertion loss of a delay line is in the order of 20 dB, a device constructed in accordance with the present invention can achieve an insertion loss in the order of 7.5 dB (increasing of course with the level of damping caused by he measured substance).

The structure described is very suitable for measuring viscosity, or for measuring the existence of certain substances in a tested environment. Coupling the input transducer to an alternating voltage source, preferably at the radio frequency (RF) range, will cause the signal to travel to the output transducer. By exposing the sensing face 360 opposite the reflective grating to liquid, whether directly or indirectly through an intermediate layer 340, a dampening effect is introduced. The dampening effect causes several changes in the wave, the most useful ones being a phase shift and a change in the insertion loss of the device. Those changes are related to the fluid viscosity, and therefore may be used for viscosity measurements. The fact that the electrical circuit is isolated from the measured liquid allows a larger variety of measurements, and enhanced reliability. However for certain devices, the sensing face 360 may be made on the same side of the reflective grating using a passivation layer for liquid phase measurements. The even energy distribution caused by the multiple local reflections allows for a wide range of viscosity range, exceeding 10,000 cP oils in a 160 MHz prototype while incurring less than 20 dB total insertion loss.

Measurement for specific substances is also accommodated by depositing a substance sensitive film or layer 350 on top of the substrate, whether directly or indirectly. The substance sensitive film may be a polymer film or other material that is chemically structured to capture specific molecules or molecule groups. When such molecules are trapped, the change in the physical properties of the film (e.g. mass, stiffness, viscosity or conductivity) cause a change in the signal propagating characteristics, which can be measured to detect the presence of such molecules. Such structure makes the sensor easily applicable to detection of even small amounts of biochemical substances by using enzyme, antibody, an antigen, or nucleic acid molecules as the coating.

Therefore, in its most preferred embodiment, the present invention is practiced in a viscometer where a single enclosure contains a multi-reflective acoustic wave device (AWD) as described above is embedded in the feedback loop of a common emitter amplifier, forming an oscillator. The oscillator (and naturally the AWD) are designed for 160 MHz. The amplifier has 18–20 dB peak gain and 20 dBm of saturated power (100 mW). Clearly, other amplifier structures may be used as known.

Power levels at the input and output of the RDL are measured utilizing temperature stable, high efficiency diode detectors, such as described in U.S. patent application Ser. No. 10/429,151, filed May $2^{nd}$ 2003. The enclosure also contains an integrated circuit thermometer, and a power regulator. Other circuitry is placed in the enclosure to achieve circuit stability and operability as known.

The substrate of the RDL in the preferred embodiment is made of Y−65° (Z+25°) cut quartz. The use of one of several predetermined thickness to wavelength ratios offers preferential coupling to a single acoustic plate mode (APM). The present embodiment uses 0.5 mm thick quartz for ruggedness and ease of handling. The preferred wavelength is 24μ. This combination offers low insertion loss in air, minimal temperature dependence, low compressional wave generation in liquids, and sensitivity to loading of the shear wave component by a viscous liquid.

Figure 4:
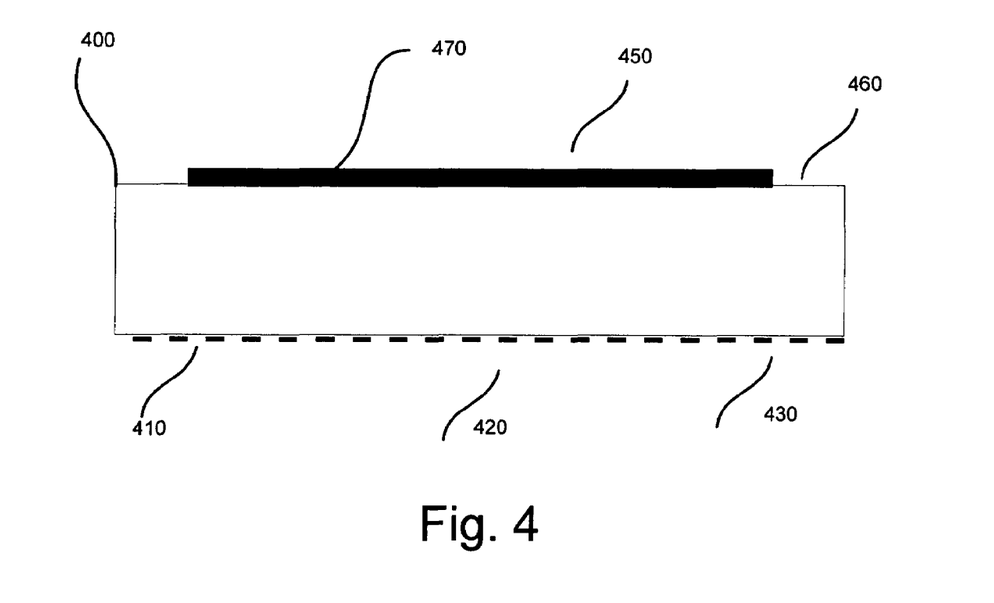
FIG. 4 depicts a simplified block diagram of a sensor utilizing an acoustic wave device in accordance with the present invention.

FIG. 4 depicts a simplified cross section of the most preferred embodiment. This embodiment uses monolithic piezoelectric substrate 400 utilizes 2-electrode-per-period transducers 410 and 430, having 1000 Å to 2000 Å aluminum metal thickness and a nominal metallization ratio of 50%±10% (equal lines and spaces), which offers an electromechanically significant transducer structure with optimized coupling into the preferred APM in the design frequency. The design uses 200 periods of electrically active transducer with 10 periods of guard electrodes on the outer extremities and 100 periods of electrically inactive intermediate reflective grating interposed between the transducers. Such an RDL exhibits an insertion loss in air of 8 dB±2 dB, at nominal design frequency of 160.4 MHz±0.25 MHz, a range of 10 dB of insertion loss dependence between air and approximately 20,000 cP mineral oil. The design affords at least 5 dB of adjacent mode rejection.

In this embodiment, the sensing face 460 of the device is located opposite to the metallized surface. The sensing face is exposed, directly or indirectly, to a liquid or gas 450. The sensing face 460 can carry a film of substance sensitive material 460 for detecting presence of specific substances of interest.

Figure 5:
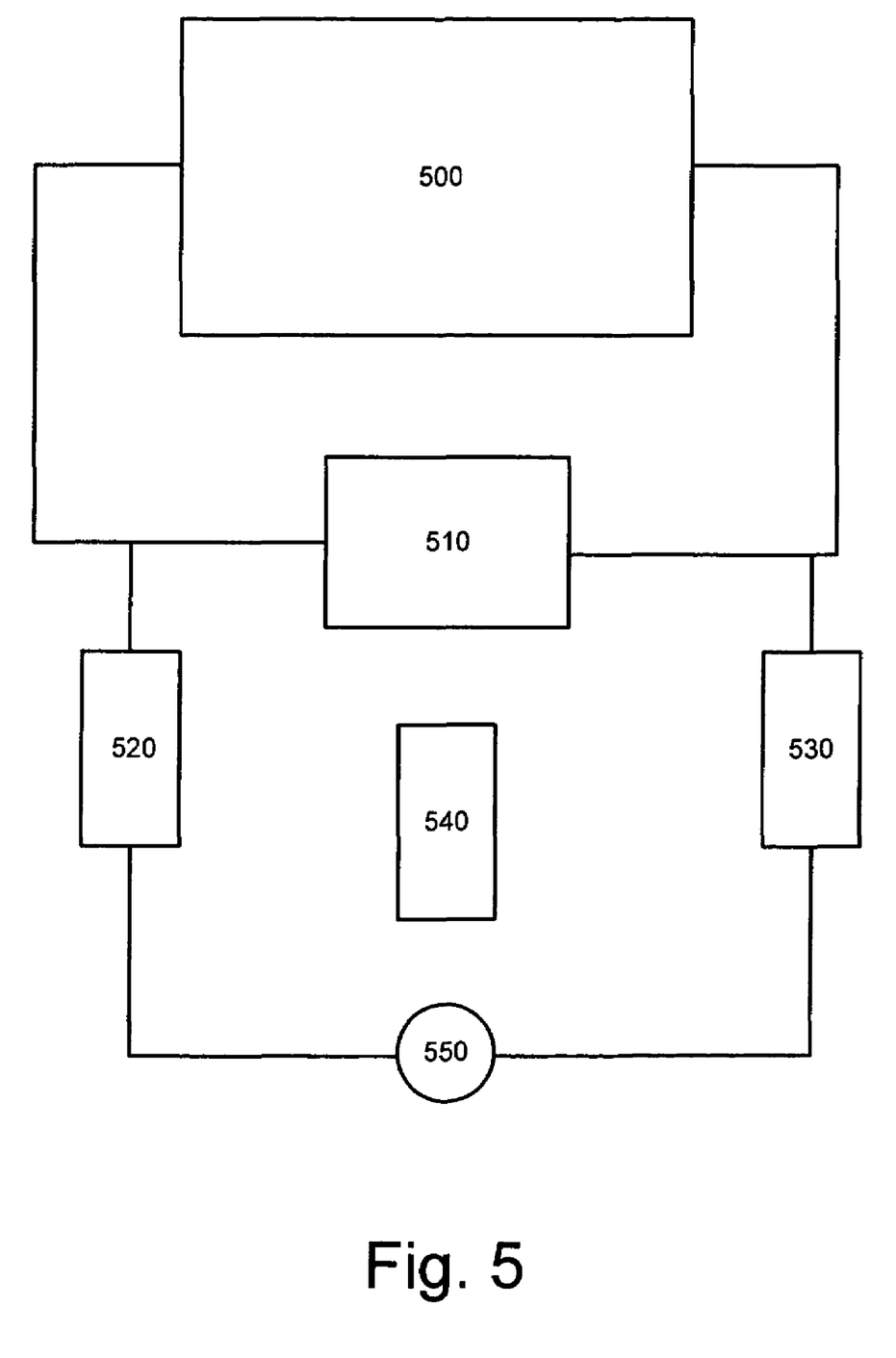
FIG. 5 represents a simplified cutout of a sensor utilizing a preferred embodiment of the invention.

FIG. 5 depicts a block diagram of a sensor utilizing the preferred embodiment. An RDL 500 is coupled to an oscillator 510 and operates as a part of its feedback loop. Diode detectors 520 and 530 detect differences in power between the input and output of the RDL. Comparator circuit 550, preferably outside the sensor enclosure, detects the differences between the input and output. While the preferred embodiment detects insertion loss, the comparator circuit may measure differences in the oscillator frequency, phase, voltage, amperage, and the like, or a combination thereof. A desirable feature is thermometer 540, which allows measurement of the ambient temperature of the sensor. In order to provide noise immunity, the sensor is also provided with a power regulator within the sensor enclosure.

While the specifications relate generally to piezoelectric substance, it will be clear to those skilled in the art that the principles described herein will operate substantially similarly with ferroelectric material. Thus the terms piezoelectric substance should be read as equivalent to, and the language in the claims should be interpreted as, relating to ferroelectric material as well. The design principles may also be applied to acoustic wave devices excited by magnetostriction, electrostriction, and Lorentz forces on current-carrying electrodes. Further the term 'crystal' should be read to extend to any type of ferroelectric or piezoelectric material, piezoelectric polymers, and the like, or to a passive solid support bearing a Lorentz force transducer.

Notably, the use of a signal sampling system comprised of a power divider, and/or buffer amplifier to extract RF signal for frequency counting, or the use of mixers to obtain data on phase shifts within the AWD, are also well known in the art, and should be considered merely a form of the comparator function.

It will be appreciated that the invention is not limited to what has been described hereinabove merely by way of example. While there have been described what are at present considered to be the preferred embodiments of this invention, it will be obvious to those skilled in the art that various other embodiments, changes, and modifications may be made therein without departing from the spirit or scope of this invention and that it is, therefore, aimed to cover all such changes and modifications as fall within the true spirit and scope of the invention, for which letters patent is applied.

What is claimed is:

1. A multi-reflective acoustic wave device comprising:
a substrate having at least one layer of piezoelectric substance having at least a first surface capable of guiding an acoustic wave, and at least a second surface opposite to said first surface;
an electromechanically significant reflective grating deposited on said first surface having a length along its longitudinal axis, said length defining longitudinal extents of an area supporting acoustic waves, wherein said active area is covered on at least 60% of its longitudinal dimension by electromechanically active transducer elements of said reflective grating, said elements being spaced at substantially periodic intervals commensurating with the wavelength of said acoustic wave;
the electromechanically active transducer elements forming an input transducer, and an output transducer, each transducer integrated into said reflective grating, and comprising a plurality of interdigitated electrodes connected in a periodic sequence to a plurality of electrical nodes;
said input transducer adapted to induce an acoustic waves, said acoustic wave having a frequency and a vector substantially perpendicularly to said electrodes and in the plane of said first surface;
wherein said reflective grating is locally continuous and periodic, and constructed to create an electromechanically significant reflective coupling between the forward and a reverse traveling acoustic wave induced in the piezoelectric substance.

2. A multi-reflective acoustic wave device as claimed in claim 1, wherein said reflective grating or a portion thereof comprises a plurality of essentially periodically repeating subgroups.

3. A multi-reflective acoustic wave device as claimed in claim 2, wherein said subgroups are independently weighted.

4. A multi-reflective acoustic wave device as claimed in claim 1 wherein each of at least the majority of the elements of said reflective grating provides a reflectivity ($\kappa/K_T$) of at least 0.1%.

5. A multi-reflective acoustic wave device as claimed in claim 1, wherein said reflective grating further comprises a substantially periodic, electrically inactive reflective structure interposed between said input and output transducers.

6. A multi-reflective acoustic wave device as claimed in claim 5, wherein said reflective structure having a length of between 25 and 150 of said periodic intervals.

7. A multi-reflective acoustic wave device as claimed in claim 5 wherein said reflective structure comprises corrugations in said piezoelectric substance.

8. A multi-reflective acoustic wave device as claimed in claim 1, wherein said reflective grating having at least one periodicity variation to introduce a offset in the phase shift between a signal coupled to said input transducer and a corresponding signal induced in said output transducer.

9. A multi-reflective acoustic wave device as claimed in claim 1, wherein at least a portion of said reflective grating comprises metal electrodes deposited on said substrate.

10. A multi-reflective acoustic wave device as claimed in claim 1, wherein at least a portion of said reflective grating comprises dielectric material deposited on said substrate.

11. A multi-reflective acoustic wave device as claimed in claim 1, wherein at least a portion of reflective grating comprises grooves cut in said substrate.

12. A multi-reflective acoustic wave device as claimed in claim 1, wherein said input transducer is a bidirectional transducer having substantially symmetrical coupling to forward and reverse acoustic waves.

13. A multi-reflective acoustic wave device as claimed in claim 1, wherein said input transducer is a unidirectional transducer having asymmetrical coupling to forward and reverse acoustic waves.

14. A multi-reflective acoustic wave device as claimed in claim 1, wherein said transducer having a length greater than or equal to 50 of said periodic intervals.

15. A multi-reflective acoustic wave device as claimed in claim 1, wherein said transducer having a length greater than or equal to 200 of said periodic intervals.

16. A multi-reflective acoustic wave device as claimed in claim 1, wherein said transducer having a dispersion curve having a stopband between 0.2% and 2% of the nominal design center frequency.

17. A multi-reflective acoustic wave device as claimed in claim 1, further comprising a propagation path interposed between said input and output transducers.

18. A multi-reflective acoustic wave device as claimed in claim 1, further comprising an amplifier circuit coupled between said input and output transducers to form an oscillator.

19. An acoustic wave device based sensor comprising:
an acoustic wave device as claimed in claim 1, further comprising a sensing face in mechanical communication with said substrate;
an oscillator circuit having an output coupled to said input transducer;
a sensing circuitry having an output, and an input coupled to said output transducer for sensing at least one parameter of a signal derived from said output transducer.

20. An acoustic wave device based sensor as claimed in claim 19, wherein said measuring circuitry comprises a comparator circuitry for detecting differences between the output of said oscillator and the output of said sensing circuitry, for detecting differences therebetween, said differences being influenced by exposure of said sensing face to a sensed substance.

21. An acoustic wave device based sensor as claimed in claim 20, wherein an output from said output transducer is coupled to said oscillator for providing feedback.

22. An acoustic wave device based sensor as claimed in claim 20, wherein said sensing circuitry and said oscillator are integrated.

23. An acoustic wave device based sensor as claimed in claim 20, wherein said comparator is adapted to measure phase difference.

24. An acoustic wave device based sensor as claimed in claim 20, wherein said comparator is adapted to measure power absorption between said input and output transducers.

25. An acoustic wave device based sensor as claimed in claim 24, further comprising a temperature compensated diode detector, for detecting said power absorption.

26. An acoustic wave device based sensor as claimed in claim 20, wherein said comparator is adapted to measure frequency change of said oscillator, induced by changes in the delay time of a signal inputted into said input transducer and outputted from said output transducer.

27. An acoustic wave device based sensor as claimed in claim 20, wherein said comparator is adapted to measure any combination of at least two parameters elected from a list of parameters consisting of phase, frequency, power, voltage, and current.

28. An acoustic wave device based sensor as claimed in claim 20, wherein said sensing face is deposited on said second surface.

29. An acoustic wave device based sensor as claimed in claim 20, further comprising a coating deposited on said sensing face.

30. An acoustic wave device based sensor as claimed in claim 29, wherein said coating comprises material selected from a list consisting of an enzyme, an antibody, a nucleic acid, an antigen, or a combination thereof.

31. An acoustic wave device based sensor a claimed in claim 20, wherein an output from said output transducer is coupled to said oscillator for providing feedback.

32. An acoustic wave device based sensor as claimed in claim 19, wherein said sensing circuitry and said oscillator are integrated.

33. An acoustic wave device based sensor as claimed in claim 19, wherein said sensing face is deposited on said second surface.

34. An acoustic wave device based sensor as claimed in claim 19, wherein said comparator is adapted to measure any combination of at least two parameters elected from a list of parameters consisting of phase, frequency, power, voltage, and current.

35. An acoustic wave device based sensor as claimed in claim 19, wherein said sensing face is adapted for exposure to liquid or gas in a manner allowing damping of a signal propagated within said substrate.

36. An acoustic wave device based sensor as claimed in claim 19 further comprising an intermediate layer deposited on said substrate, wherein said sensing face comprises a face of said intermediate layer.

37. An acoustic wave device based sensor as claimed in claim 19, further comprising a passivation layer deposited on said sensing face.

38. An acoustic wave device based sensor as claimed in claim 19, further comprising a substance sensitive layer on top of said sensing face, said substance sensitive layer is being chemically structured to change at least one physical property thereof responsive to presence of predetermined molecules or molecule groups.

39. An acoustic wave device based sensor as claimed in claim 19, further comprising a coating deposited on said sensing face.

40. An acoustic wave device based sensor as claimed in claim 39, wherein said coating comprises material selected from a list consisting of an enzyme, an antibody, a nucleic acid, an antigen, or a combination thereof.

41. An acoustic wave device based sensor as claimed in claim 19 further comprising temperature compensation circuitry for compensating measured parameters in accordance to temperature.

42. An acoustic wave device based sensor as claimed in claim 19 further comprising temperature compensation software, for compensating measured parameters in accordance to temperature.

43. A sensor tolerant of viscous dampening comprising:
an acoustic wave device as claimed in claim 1, further comprising a sensing face in mechanical communication with said substrate;
an oscillator circuit having an output coupled to said input transducer;
a first diode detector electrically coupled to the input transducer, and a second diode detector electrically coupled to said output transducer, for providing power sensing.

44. A sensor as claimed in claim 43, wherein said diode detectors are temperature compensated.

45. A sensor as claimed in claim 43 further comprising a temperature sensor to sense ambient temperature.

46. A sensor as claimed in claim 43 further comprising a voltage regulator.

47. A sensor as claimed in claim 43 wherein said acoustic wave device acts as a portion of a feedback loop for said oscillator.

48. A sensor as claimed in claim 43 wherein said sensing face is said second surface or a portion thereof.

49. A sensor as claimed in claim 48, and further comprising an intermediate layer between said sensing face and a liquid to be measured.

50. An acoustic wave device based sensor as claimed in claim 43, further comprising a coating deposited on said sensing face.

51. An acoustic wave device based sensor as claimed in claim 50, wherein said coating comprises material selected from a list consisting of an enzyme, an antibody, a nucleic acid, an antigen, or a combination thereof.

52. A multi-reflective acoustic wave device as claimed in claim 1, wherein said active area is covered on at least 67% of its longitudinal dimension by electromechanically active transducer elements of said reflective grating.

53. A multi-reflective acoustic wave device as claimed in claim 1, wherein said active area is covered on at least 70% of its longitudinal dimension by electromechanically active transducer elements of said reflective grating.

54. A multi-reflective acoustic wave device as claimed in claim 1, wherein said active area is covered on at least 77% of its longitudinal dimension by electromechanically active transducer elements of said reflective grating.

55. A multi-reflective acoustic wave device as claimed in claim 1, wherein said active area is covered on at least 80% of its longitudinal dimension by electromechanically active transducer elements of said reflective grating.

56. A multi-reflective acoustic wave device as claimed in claim 1, wherein said active area is covered on 100% of its longitudinal dimension by electromechanically active transducer elements of said reflective grating.

* * * * *